(12) United States Patent
Papadimitrakopoulos et al.

(10) Patent No.: US 9,101,301 B2
(45) Date of Patent: Aug. 11, 2015

(54) CONTROL OF BIOFOULING IN IMPLANTABLE BIOSENSORS

(75) Inventors: Fotios Papadimitrakopoulos, West Hartford, CT (US); Santhisagar Vaddiraju, Willimantic, CT (US)

(73) Assignee: THE UNIVERSITY OF CONNECTICUT, Farmington, CT (US)

( * ) Notice: Subject to any disclaimer, the term of this patent is extended or adjusted under 35 U.S.C. 154(b) by 335 days.

(21) Appl. No.: 13/586,436

(22) Filed: Aug. 15, 2012

(65) Prior Publication Data

US 2013/0213110 A1    Aug. 22, 2013

Related U.S. Application Data

(60) Provisional application No. 61/523,597, filed on Aug. 15, 2011.

(51) Int. Cl.
| | |
|---|---|
| *A61B 5/145* | (2006.01) |
| *A61B 5/1459* | (2006.01) |
| *A61B 5/1486* | (2006.01) |
| *A61B 5/1495* | (2006.01) |
| *C12Q 1/00* | (2006.01) |
| *G01N 33/52* | (2006.01) |

(52) U.S. Cl.
CPC ............ *A61B 5/145* (2013.01); *A61B 5/1459* (2013.01); *A61B 5/1495* (2013.01); *A61B 5/14503* (2013.01); *A61B 5/14865* (2013.01); *C12Q 1/001* (2013.01); *G01N 33/52* (2013.01); *A61B 2562/18* (2013.01); *A61B 2562/247* (2013.01)

(58) Field of Classification Search
CPC ............ A61B 5/14503; A61B 5/1473; A61B 5/14865; A61B 2562/02; A61B 2562/12; A61B 2562/16; A61M 2230/20–2230/208; A61M 2205/04; A61M 2202/0064; A61M 2202/0078; A61L 2300/60–2300/61; A61L 33/06–33/128; A61L 31/04–31/06; A61L 31/08; A61L 31/10; A61L 2400/08
USPC ................................ 422/422–426, 484–488; 204/403.01–403.15; 605/908, 910
See application file for complete search history.

(56) References Cited

U.S. PATENT DOCUMENTS 7,828,728 B2    11/2010  Boock et al.
2006/0257996 A1 *  11/2006  Simpson et al. ........... 435/287.2
(Continued)

FOREIGN PATENT DOCUMENTS

WO      2006018425 A2     2/2006

OTHER PUBLICATIONS

International Search Report for PCT/US2012/050939, International Filing Date Aug. 15, 2012, date of mailing Feb. 28, 2013, 6 pages.
(Continued)

*Primary Examiner* — J. Christopher Ball
(74) *Attorney, Agent, or Firm* — Cantor Colburn LLP (57) ABSTRACT

Disclosed herein is a device comprising a biosensor having disposed upon it a coating; the coating comprising a polymer matrix; where the polymer matrix is operative to facilitate the inwards and outwards diffusion of analytes and byproducts to and from the sensing element of the biosensor; and a sacrificial moiety; the sacrificial moiety being dispersed in the polymer matrix, where the sacrificial moiety erodes with time and increases the porosity of the polymer matrix thus offsetting decreases in analyte permeability as a result of biofouling.

27 Claims, 8 Drawing Sheets

(56) References Cited

U.S. PATENT DOCUMENTS

2007/0131549 A1* 6/2007 Cai et al. .................. 204/403.02
2009/0280155 A1 11/2009 Chappa et al.

OTHER PUBLICATIONS

Written Opinion for PCT/US2012/050939, International Filing Date Aug. 15, 2012, date of mailing Feb. 28, 2013, 6 pages.
International Preliminary Report on Patentability for PCT/US2012/050939, International Filing Date Aug. 15, 2012, date of mailing Feb. 27, 2014, 8 pages.
Bhardwaj et al., "A Review of the development of a Vehicle for Localized and Controlled Drug Delivery for Implantable Biosensors", Journal of Diabetes Science and Technology, vol. 2, Issue 6, Nov. 2008, pp. 1016-1027.
International Search Report and the Written Opinion of the International Searching Authority for PCT/US012/060929, date of mailing Feb. 28, 2013, 6 pages.
Written Opinion of the Internatioanl Searching Authority for PCT/US2012/050939, date of mailing Feb. 28, 2013, 6 pages.

* cited by examiner

CONTROL OF BIOFOULING IN IMPLANTABLE BIOSENSORS

CROSS-REFERENCE TO RELATED APPLICATIONS

This disclosure claims priority to U.S. Provisional Application No. 61/523,597 filed on Aug. 15, 2011, the entire contents of which are hereby incorporated by reference.

FEDERAL RESEARCH STATEMENT

This invention was made with Government support under Agreement No. W81XWH-07-1-0688. The U.S. Government has certain rights in the invention.

BACKGROUND

This disclosure relates to control of biofouling in implantable biosensors. In particular, this disclosure relates to a biofouling inhibiting coating for a biosensor that may be installed inside the body of a living being.

Miniaturized, implantable biosensors form an important class of biosensors because of their ability to continuously monitor metabolite(s) level(s) without the need for patient intervention and regardless of the patient's physiological state (rest, sleep, exercise, and the like). Such continuous monitoring is important for the treatment of certain diseases such as Diabetes Mellitus and to avoid associated complications such as obesity, renal failure and blindness. However, the development of these implantable biosensors have been impeded since they are not capable of reliable in vivo monitoring for longer than a few hours without the need for repeated calibration.

Figure 1:
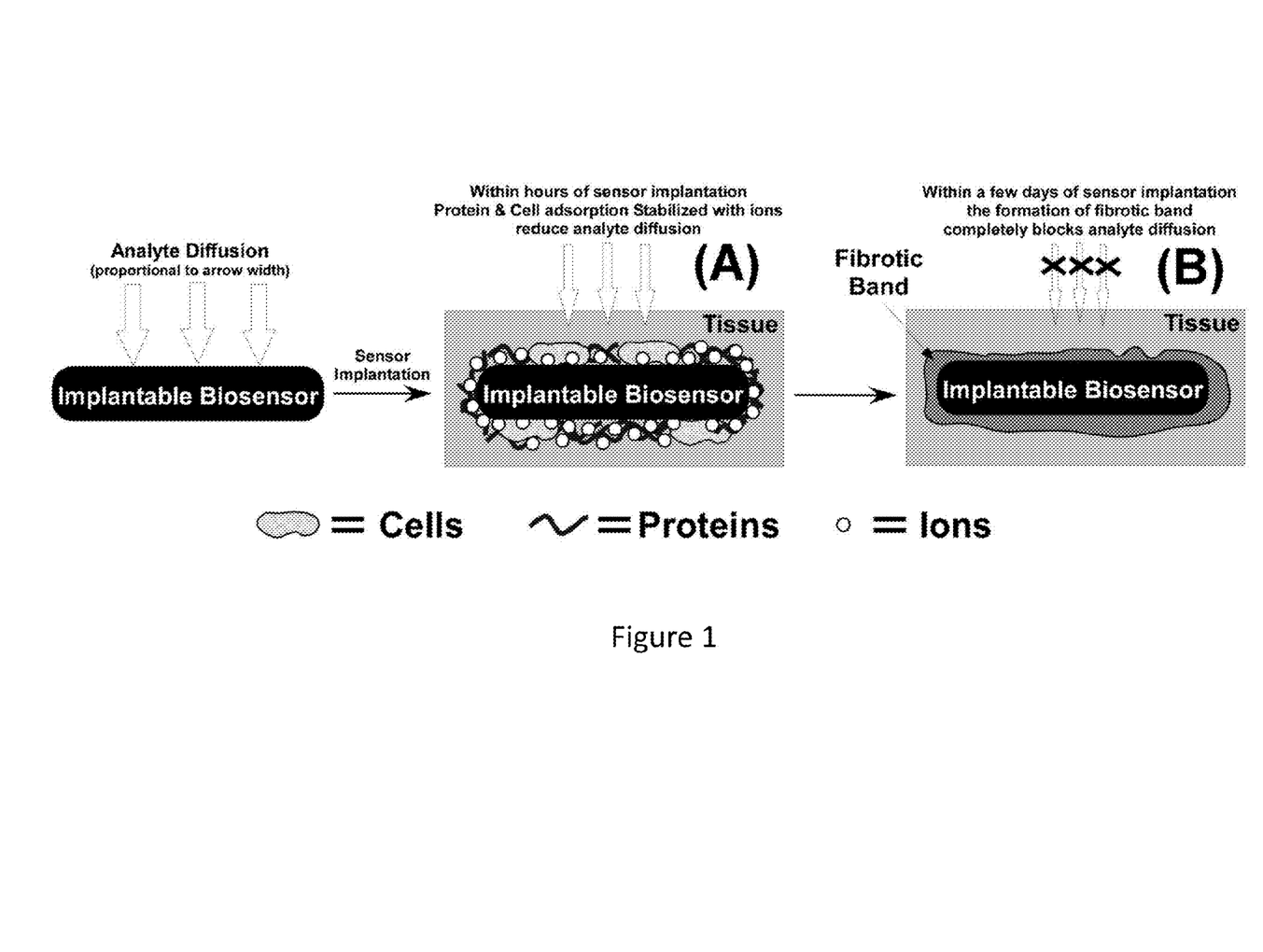
FIG. 1A is a schematic representation of the process of biofouling following sensor implantation.
FIG. 1B is a depiction of one of the effects of biofouling which leads to the formation of fibrotic band that completely blocks analyte diffusion to the implantable biosensor.

This instability is considered to be a result of a constantly changing in vivo environment that these sensors experience following their implantation. Tissue inflammation and foreign body response sets in within short periods of time after sensor implantation. While the former is caused by the tissue injury that results from implantation of the device as well as the continual presence of the device in the body, the latter is a result of the body's natural response to ultimately encapsulate the implanted device with fibrotic tissue and prevent it from interacting with the surrounding tissue. FIG. 1 is a schematic representation of the process of biofouling (A) following sensor implantation. Such biofouling eventually signals a cascade of events to lead to the formation of fibrotic band (B), which completely blocks analyte diffusion to the implantable biosensor.

Along with these processes, the implanted sensor is continuously inundated with low molecular weight proteins (in the order of few KDa) along with cells (in the order of 10 to 100 microns) within a short period of time following implantation. The small molecular weight proteins penetrate and clog the sensor membrane(s) while the cells deposit on the outer sensor surface (FIG. 1(B)). These two actions cause a severe mass transfer barrier for analyte diffusion to the sensing element, thereby degrading the in vivo sensor performance and long-term stability. Such degradation in sensor performance typically necessitates periodic sensor calibration using an external analyte monitoring device via finger pricking.

In order to alleviate the issue of in vivo sensor degradation, various biocompatible coatings (such as Nafion, hyaluronic acid, humic acids, phosphorylcholine, 2-methacryloyloxyethyl phosphorylcholine, polyurethanes with phospholipid polar groups, poly vinyl alcohol hydrogels, betaines, and the like) have been employed. These membranes are intended to: (i) maintain a desired, yet constant flux of passage of analyte molecules over long periods of time, (ii) reduce protein adsorption, and (iii) promote integration of the sensor with the surrounding tissues. However, the success of these strategies is ultimately impeded by the action of multi-valent ions that in combination with flexible and charged, low molecular weight protein fragments and large charged cell deposits forms stable complexes that are difficult to dissociate within the restrained environments of either inner membranes or outer membrane/tissue interface.

In another approach, "textured" rather than "smooth" implant surfaces have been employed in order to mitigate biofouling. This arises from the fact that nanostructured membranes have a different contact angle and therefore a different degree of hydrophobicity/hydrophilicity from a regular smooth membrane which repels the adsorption of large charged cells onto the surface of the implant. However, these methodologies are costly and difficult to be implemented in conjunction with the miniaturization requirements of an implantable device. Moreover, the possible toxicity of the nanostructured materials used to create textured surfaces is a concern and can cause an enormous increase in regulatory burden.

Researchers have also pursued smart nanoporous materials that change their permeability in response to environmental stimuli such as pH, temperature ionic/solute concentration, as well as magnetic and electric fields. Most of these smart nanoporous materials work on the basis of reversible expansion and collapse of responsive polymers incorporated within their pores. An extension to this approach has been the incorporation of magnetostrictive materials to induce local oscillating/vibrational motions upon the application of external stimuli. Both these methodologies are intended to cause protein desorption. However, the incorporation of such elements are proven costly and difficult, especially considering the desire for miniaturization of all implantable systems. Moreover, the possible toxicity of these nanomaterials is undetermined and could increase regulatory burden.

In yet another attempt at mitigating bioadhesion of tissue to the biosensor, proteases have been incorporated into a variety of different matrices to reduce the binding of proteins to surfaces by degrading adsorbed biomolecules. However, considering the large matrix of proteins available in the human physiology and the confined space of the outer membrane, their ability to yield a 100% efficacy is compromised. Moreover, the inherent stability of these proteases is also of a concern.

More recently nanocomposite coatings where nanomaterials are embedded within in a polymer matrix are also being used to reduce biofouling. Nanocomposite coatings based on carbon nanotubes and silica nanoparticles have been used to reduce biofouling. However, the success of these approaches has been limited so far. Similarly, the toxicity of these nanomaterials is questionable and can increase the regulatory burden.

In yet another approach, microsphere-based drug-delivery coatings have been utilized to reduce inflammation via localized delivery of anti-inflammatory drugs. These coatings, while capable of minimizing mid and long-term tissue inflammation and fibrotic encapsulation, they are unable to mitigate the short-term effects from protein and cell adsorption. Consequently, the issue of protein biofouling and cell adhesion remains to be a problem which leads to constant changes in analyte permeability over the entire duration of in vivo sensor operation.

SUMMARY

Disclosed herein is a device comprising a biosensor having disposed upon it a coating; the coating comprising a polymer matrix; where the polymer matrix is operative to facilitate an inwards diffusion of analytes towards a sensing element of the biosensor as well as the outwards diffusion of byproducts and various tissue response modifying (TRM) drug; and a sacrificial moiety; the sacrificial moiety being dispersed in the polymer matrix, where the sacrificial moiety erodes with time and increases the porosity of the polymer matrix thus offsetting decreases in analyte permeability as a result of biofouling.

Disclosed herein too is a method of manufacturing a biosensor comprising a coating on a biosensor; the coating comprising a polymer matrix; where the polymer matrix is operative to facilitate an inwards diffusion of analytes towards a sensing element of the biosensor; and a sacrificial moiety; the sacrificial moiety being dispersed in the polymer matrix, where the sacrificial moiety erodes with time and increases the porosity of the polymer matrix thus offsetting decreases in analyte permeability as a result of biofouling.

Disclosed herein too is an analyte-sensing device capable of reliable sensing in a biofouling-prone media comprising a sensing element; a self sealing layer disposed on the sensing element capable of allowing diffusion of electro-active species towards the sensing element; where the self sealing layer is not prone to swelling and is intimately bonded to the sensing element; one or more layers comprising enzymes that are disposed upon the self-sealing layer; selectively the enzymes being operative to convert an analyte of interest to an electro-active species; where the electro-active species diffuses through the self sealing layer to produce a detectable signal proportional to a concentration of the analyte; a second layer disposed upon the one or more layers that comprises enzymes; the second layer being operative to limit diffusion of the analyte and control diffusion towards the sensor of molecules with size larger than that of the analyte; a third layer comprising a composite coating that comprises a polymer matrix and a sacrificial moiety; where the polymer matrix is operative to facilitate an inwards diffusion of analytes towards the sensing element; and wherein the sacrificial moiety is dispersed in the polymer matrix, where the sacrificial moiety erodes with time and increases the porosity of the polymer matrix thus offsetting decreases in analyte permeability as a result of biofouling.

Disclosed herein too is a method to realize an internal self-calibration of an implantable biosensor, the biosensor comprising two sensing elements; where self calibration of the biosensor is achieved through differential measurement of background currents obtained from the two sensing elements; where one of the sensing elements is encased in an outer composite membrane, while the other of the said sensing element is intentionally left blank; the said outer composite membrane comprises a polymer matrix and a sacrificial moiety; where the polymer matrix is operative to facilitate an inwards diffusion of analytes towards the sensing element; and wherein the sacrificial moiety is dispersed in the polymer matrix, where the sacrificial moiety erodes with time and increases the porosity of the polymer matrix thus offsetting decreases in analyte permeability as a result of biofouling.

BRIEF DESCRIPTION OF THE FIGURES

FIG. 2 (A)-(D) is an exemplary schematic that depicts the methodology that is used to reduce biofouling in implantable biosensors;

FIGS. 3 (A)-(D) shows a variety of biodegradable beads;

DETAILED DESCRIPTION

Disclosed herein is a biofouling inhibiting coating for a biosensor that is installed inside the body of a living being. The biofouling inhibiting coating can be used to reduce biofouling in implantable biosensors via the creation of fresh-void-space within the outer membrane that gradually becomes rigid via biofouling, thereby preventing the complete collapse onto the fresh-void-space. It also offsets any biofouling-induced permeability changes by increasing membrane permeability. It re-establishes analyte transport within the outer membrane via creation of new sensor/tissue interface and is able to tune the magnitude of fresh-void-space in order to offset in vivo loss of sensor sensitivity. It also affords a methodology to realize a calibration-free implantable biosensor. Disclosed herein too is a method of manufacturing the biofouling inhibiting coating for biosensors that are installed inside the body of living beings.

Figure 2:
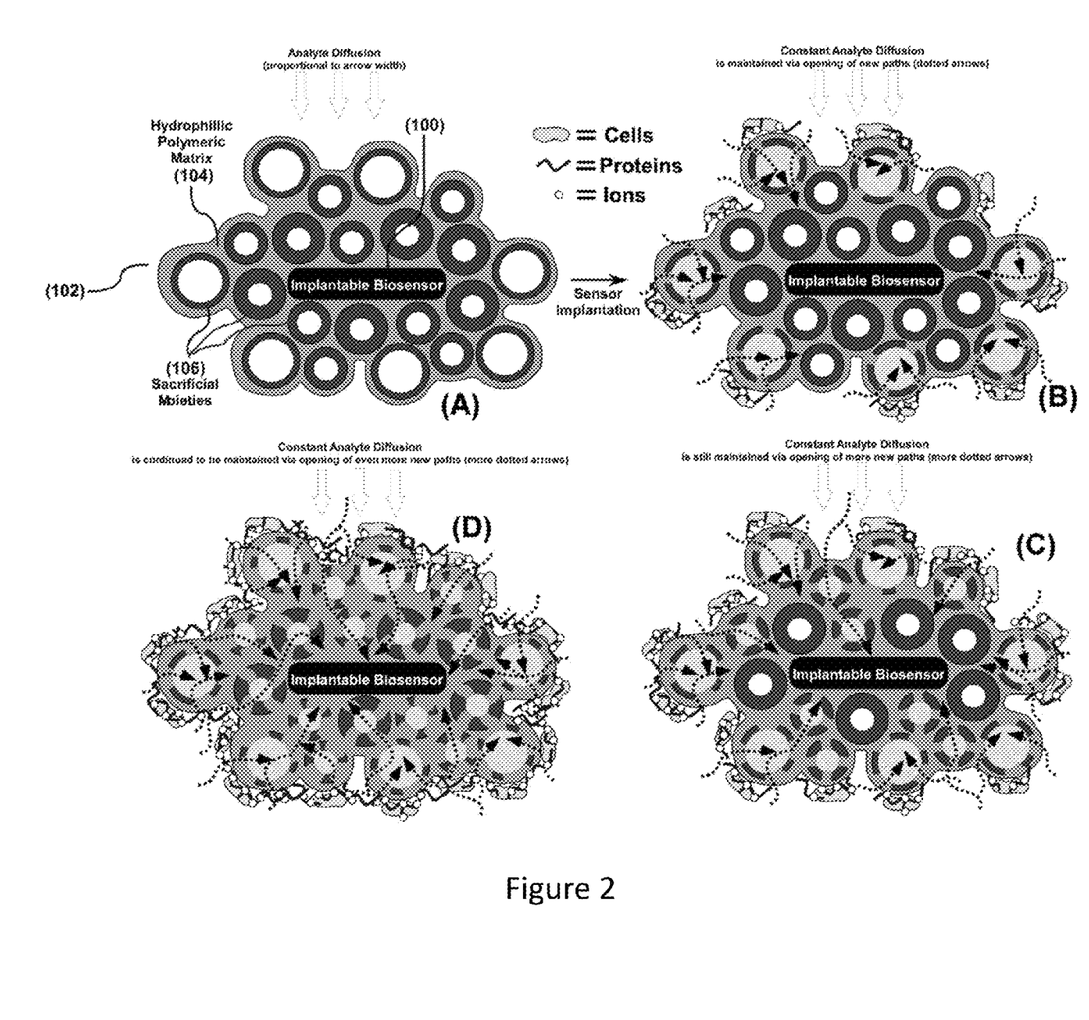

FIG. 2 (A)-(D) is an exemplary schematic that depicts the methodology that is used to reduce biofouling in implantable biosensors. As shown in FIG. 2a, an implantable biosensor 100 is coated by a composite membrane 102 comprising a hydrophilic polymeric matrix 104 that is liable for the inwards diffusion of analytes towards the implantable biosensor 100 and an assortment of sacrificial moieties 106. In the FIG. 2 (A)-(D), the implantable biosensor is encased within a hydrophilic polymeric matrix that contains sacrificial moieties with internal free space (A). These sacrificial moieties are structured in such a way that they erode at different timescales, as schematically shown with varying layer thickness. Following sensor implantation, the gradual biofouling buildup is constantly offset by the constant increase of fresh-void-space by eroding a greater number of sacrificial moieties (See FIGS. 2 (B), (C), and (D).

The hydrophilic polymeric matrix comprises hydrogels, xerogels, organogels, absorbent polymers, dip-coated or layer-by-layer coated polyelectrolytes, electropolymerized polymers, or the like, that forms a continuous pathway for diffusion of analyte and other byproducts. The hydrophilic polymeric matrix 104 may be selected from a wide variety of thermoplastic resins, blend of thermoplastic resins, thermosetting resins, or blends of thermoplastic resins with thermosetting resins. The hydrophilic polymeric matrix 104 may also be a blend of polymers, copolymers, terpolymers, or combinations comprising at least one of the foregoing organic polymers. The hydrophilic polymeric matrix 104 can also be an oligomer, a homopolymer, a copolymer, a block copolymer, an alternating block copolymer, a random polymer, a random copolymer, a random block copolymer, a graft copolymer, a star block copolymer, a dendrimer, or the like, or a combination comprising at last one of the foregoing polymers.

Examples of the hydrophilic polymers for use in the matrix 104 are polyacrylates, polyacrylamides, polyvinylacetates, polyvinyl acetamides, polyvinyl alcohols, neutralized and un-neutralized polymeric acids (e.g., neutralized and un-neutralized polyacrylics acids, neutralized and un-neutralized polysulfonic acids, neutralized and un-neutralized polystyrene sulfonic acids, or the like) polydiallyl dimethyl ammonium chlorides, poly(1-glycerol methacrylate)s, poly(2-dimethylaminoethyl methacrylate)s, poly(2-ethyl-2-oxazoline), poly(2-hydroxyethyl methacrylate/methacrylic acid)s, poly(2-hydroxypropyl methacrylate)s, poly(2-methacryloxyethyltrimethylammonium halide)s, poly(2-vinyl-1-methylpyridinium halide)s, poly(2-vinylpyridine N-oxide)s, poly(2-vinylpyridine)s, poly(3-chloro-2-hydroxypropyl-2-methacryloxyethyldimethylammonium chloride)s, or the like, or a combination comprising at least one of the foregoing water soluble polymers.

In one embodiment, the polymer can comprise one or more of the foregoing water soluble polymers and a synthetic polymer that is hydrophobic so long as the resulting polymer is swellable in the carrier fluid. In an exemplary embodiment, the polymer can comprise one or more of the foregoing water soluble polymers and a synthetic polymer that is hydrophobic so long as the resulting polymer is swellable in an aqueous carrier fluid. The foregoing water soluble polymers can be copolymerized or blended with the hydrophobic synthetic polymer.

Examples of hydrophobic synthetic polymers are polyacetals, polyolefins, polycarbonates, polystyrenes, polyesters, polyamides, polyamideimides, polyarylates, polyarylsulfones, polyethersulfones, polyphenylene sulfides, polyvinyl chlorides, polysulfones, polyimides, polyetherimides, polytetrafluoroethylenes, polyetherketones, polyether etherketones, polyether ketone ketones, polybenzoxazoles, polyphthalides, polyacetals, polyanhydrides, polyvinyl ethers, polyvinyl thioethers, polyvinyl ketones, polyvinyl halides, polyvinyl nitriles, polyvinyl esters, polysulfonates, polysulfides, polythioesters, polysulfones, polysulfonamides, polyureas, polyphosphazenes, polysilazanes, polyethylene terephthalate, polybutylene terephthalate, polyurethane, polytetrafluoroethylene, polychlorotrifluoroethylene, polyvinylidene fluoride, polyoxadiazoles, polybenzothiazinophenothiazines, polyoxothiazoles, polypyrazinoquinoxalines, polypyromellitimides, polyquinoxalines, polybenzimidazoles, polyoxindoles, polyoxoisoindolines, polydioxoisoindolines, polytriazines, polypyridazines, polypiperazines, polypyridines, polypiperidines, polytriazoles, polypyrazoles, polypyrrolidines, polycarboranes, polyoxabicyclononanes, polydibenzofurans, polyphtalides, polyacetals, polyanhydrides, polyvinyl ethers, polyvinyl thioethers, polyvinyl ketones, polyvinyl halides, polyvinyl nitriles, polyvinyl esters, polysulfonates, polysulfides, polythioesters, polysulfones, polysulfonamides, polyureas, polyphosphazenes, polysilazanes, polysiloxanes, polyolefins, or the like, or a combination comprising at least one of the foregoing hydrophobic synthetic polymers.

The hydrophilic polymer can comprise a blend or a copolymer of a synthetic polymer and a naturally occurring polymer. Examples of naturally occurring hydrophilic polymers include polysaccharides, derivatives of polysaccharides (e.g., hydroxyethyl guar (HEG), carboxymethyl guar (CMG), carboxyethyl guar (CEG), carboxymethyl hydroxypropyl guar (CMHPG), cellulose, cellulose derivatives ((i.e., derivatives of cellulose such as hydroxyethylcellulose (HEC), hydroxypropylcellulose (HPC), carboxymethylcellulose (CMC), carboxyethylcellulose (CEC), carboxymethyl hydroxyethyl cellulose (CMHEC), carboxymethyl hydroxypropyl cellulose (CMHPC)), karaya, locust bean, pectin, tragacanth, acacia, carrageenan, alginates (e.g., salts of alginate, propylene glycol alginate, and the like), agar, gellan, xanthan, scleroglucan, or the like, or a combination comprising at least one of the foregoing naturally occurring hydrophilic polymers.

In one embodiment, the hydrophilic polymeric matrix is loaded with sacrificial moieties, which are prone to erosion when exposed to physiological fluids containing enzymes that stimulate erosion or by external stimuli such as localized heat, changes in pH, light irradiation, or the like. The polymeric matrix is selected so that it remains intact after the erosion of the sacrificial moieties and experiences either 'no' collapse or a 'partial' collapse, depending on its modulus and crosslink density. To this effect, the non-specific adsorption of proteins, protein fragments, ions, small molecular weight compounds within the internal nanostructure of the hydrophilic matrix will also increase their stiffness, hence prevent their complete collapse onto the freshly generated void-space.

Upon sensor implantation in the body of a living being, the natural processes of biofouling commences in which the adsorption of proteins, ions and cells begin to coat the surface and possibly penetrate deeper depending on the membrane porosity. At the same time, the erosion of sacrificial moieties gets initiated, which would result in generation of fresh-void space that progressively increases membrane porosity (FIGS. 2(B)-2(D). In addition, the erosion of these sacrificial moieties can be programmed to lead to creation of: new sensor/tissue interface that desorbs the bound proteins and ions and thereby re-establishes analyte flux; and/or fresh sensor/outer membrane/tissue interface(s) that are less prone to protein and ion adsorption. All these effects, with the help of underlying sensing element(s) can also actively calibrate the implantable biosensor against the negative effects of protein biofouling and eventual sensor degradation.

The sacrificial moieties can comprise polymersomes, colloidosomes, polymeric microspheres, block copolymers, interpenetrating networks, filled composites, polymer coated nanoparticles, nanoplatlets, nanorods, polymer coated salt crystals, self-assembled polymer spheres, or the like, or a combination comprising at least one of the foregoing sacrificial moieties.

Figure 3:
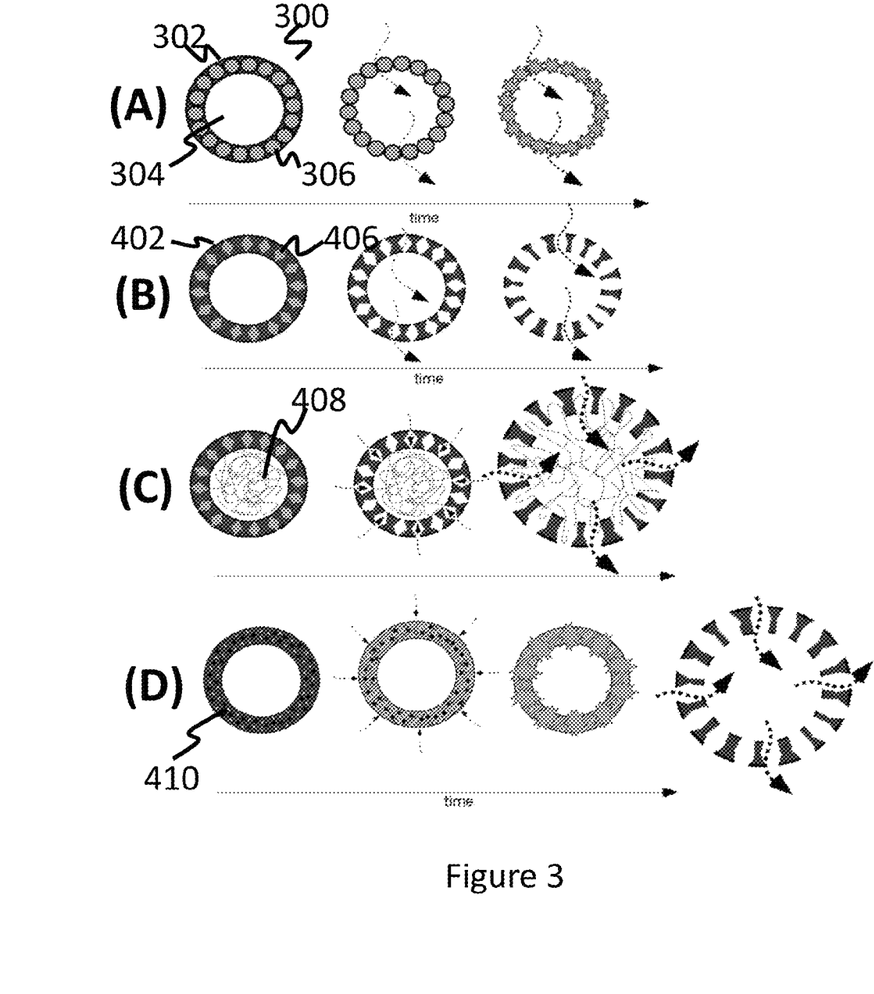

FIGS. 3 (A)-(D) shows a variety of biodegradable beads. FIG. 3(A) depicts colloidosome-based hollow particles 300 comprising biodegradable polymeric beads 302. The colloidosomes-based hollow particles can be used to control biofouling. Colloidosomes wherein an inner hollow core 304 is surrounded by hydrophobic bead like structures 306 can be used to tune the rate of change of membrane permeability. Upon implantation in the body of a living being, the outer hydrophobic beads will rapidly erode, exposing the inner hollow core and increasing the fresh-void-space. Depending on the type, loading and size of these beads, a unique rate of change of membrane permeability can be achieved that can in turn complement the permeability changes due to biofouling. Examples of biodegradable polymers for use in the beads are poly lactic acid (PLA), poly glycolic acid (PGA), polylactic-glycolic acid (PLGA), polyaspirin, polyanhydride, poly-caprolactone (PCL), copolymers of polylactic-glycolic acid and poly-caprolactone (PCL-PLGA copolymer), polyhydroxybutyrate-valerate (PHBV), polyorthoester (POE), polyethylene oxide-butylene terephthalate (PEO-PBTP), poly-D,L-lactic acid-p-dioxanone-polyethylene glycol block copolymer (PLA-DX-PEG), poly(anhydrides) or the like, or combinations comprising at least one of the foregoing biodegradable polymers. In one embodiment, the biodegradable polymer may be used to form the beads as well as the matrix that holds the beads together.

In one embodiment, the colloidosome-based hollow particles comprise a labile group that is operative to facilitate degradation of the polymer upon activation of the labile group. It is desirable for the labile group to be water soluble or otherwise soluble in the bodily fluids (which are generally aqueous). Labile groups include ester groups, amide groups, carbonate groups, azo groups, disulfide groups, orthoester groups, acetal groups, etherester groups, ether groups, silyl groups, phosphazine groups, urethane groups, esteramide groups, etheramide groups, anhydride groups, and any derivative or combination thereof. In some embodiments, the labile links are derived from oligomeric or short chain molecules that include poly(anhydrides), poly(orthoesters), orthoesters, poly(lactic acids), poly(glycolic acids), poly(caprolactones), poly(hydroxybutyrates), polyphosphazenes, poly(carbonates), polyacetals, polyetheresters, polyesteramides, polycyanoacrylates, polyurethanes, polyacrylates, or the like, or a combination comprising at least one of the foregoing oligomeric or short chain molecules. In some embodiments, the labile links may be derived from a hydrophilic polymeric block comprising at least one compound selected from the group consisting of a poly(alkylene glycol), a poly(alcohol) made by the hydrolysis of polyvinyl acetate), a poly(vinyl pyrrolidone), a polysaccharide, a chitin, a chitosan, a protein, a poly(amino acid), a poly(alkylene oxide), a poly(amide), a poly(acid), a polyol, any derivative, copolymer, or combination thereof.

In one embodiment, in one method of using the colloidosome-based hollow particles 300 to control biofouling, as the outer layer or shell (hydrophobic bead like structures 306) swells upon being contacted by body fluids, the space between the polymer beads open up to afford analyte diffusion. Following partial or complete degradation of the biodegradable polymer beads, the analyte permeability further increases.

In another embodiment depicted in the FIG. 3(B), nano- or micro-crystal-containing polymersomes may be used to control biofouling around the biosensor. FIG. 3(B) depicts polymersome-based hollow particles 300 comprising biodegradable polymeric beads 402. The polymersome-based hollow particles are somewhat similar to the structure of the colloidosome-based hollow particles 300 except that the biodegradable beads are now replaced with nano- or microcrystals. Polymersomes therefore comprise an inner hollow core 304 surrounded by nano- or microcrystals that are hydrophobic bead like structures 406 that can be used to tune the rate of change of membrane permeability.

In one embodiment, in one method of using polymersome-based hollow particles 300, the crystalline domains dissolve upon contacting body fluids. This opens up fissures, followed by further shell degradation that enhances analyte diffusion. In another embodiment, in another method of using polymersome-based hollow particles 300, light-, temperature- or enzymatic-induced depolymerization of a biodegradable polymer incorporated within the shell may be undertaken, so that analyte permeability is increased. Biofouling can thus be controlled by either having the crystals in the shell dissolve or by having the matrix that holds the crystals together degrade or dissolve.

In another embodiment, both of the foregoing methods employed in the polymersome-based hollow particles can be jointly employed. In other words, the erosion of sacrificial moieties can occur in an 'onion-like' configuration where erosion progresses from outside to inside.

In yet another embodiment, depicted in the FIG. 3(C), the initial polymersome contains a dried hydrophilic polymer 408 in its core. As the shell 302 degrades, water infuses into the core to swell the dried hydrophilic polymer that results in substantial expansion of the polymersome volume to not only increase analyte diffusion but also rupture assemblies of the adsorbed proteins, cells and ions as well as create new sensor/tissue interface.

In yet another embodiment, the initial polymersome contains polymer-coated reactive intermediates (species) 410 within the shell. As the outer shell 302 degrades, the reactive species within the reactive centers 410 interact with either each other or their surrounding aqueous environment to release gases whose volume is considerably larger than the volume of the reactive center. Such reactions generate significant amounts of fresh-void-space that can break up and exfoliate large structures of adsorbed proteins, ions and cells from the surface of their outer membrane. Exemplary reactive centers are polymer coated metal nanoparticles (K, Na, Ca, Fe, Mg) that upon polymer degradation oxidize to release hydrogen gas, oxygen generating enzymes that when come in contact with their substrate (also encapsulated as different reactive species), rapidly generate oxygen gas.

In summary, in all the aforementioned scenarios depicted in the FIGS. 3(A)-3(D), the core can be empty or filled (partially or completely). When the core is filled it can be filled with a composition that has the same composition as the shell. Alternatively, it can be filled with a composition that has a different composition from that of the outer shell.

This invention is particularly suitable for realizing a calibration-free biosensor that can be installed inside the body of a living being. This biosensor must have the ability to progressively limit the diffusion of larger molecular weight species towards the working electrode. In order to achieve this, it is possible to coat the working electrode of an electrochemical sensor (i.e. optical, fluorescent, electronic, magnetic, and the like) with a series of layers affording the following functions in the order described:

A first layer (i.e., a very tight, self-sealing thin membrane (not shown)), capable of allowing diffusion of molecule smaller than $H_2O_2$ (i.e., water, oxygen, $H^+$, $OH^-$, and the like.) and excluding any larger molecules from direct contact with the sensing element (i.e., working electrode). This membrane can be an electropolymerized film (such as polyphenol, poly(phenylene diamine), polypyrrole, polysiloxanes and the like), that is not prone to swelling. This film aside from imparting high sensor selectivity also prevents the deposition of contaminants onto the working electrode in the unlikely event that they pass through the various outer layers of the sensor. This layer should have good adhesion to the electrode.

A second layer or layers of one or multiple enzymes that selectively convert(s) the analyte of interest to an electroactive species such as $H_2O_2$ to diffuse through the first layer so that it can produce a detectable signal. This layer or layers should not be prone to swelling and retain good adhesion with the first layer.

A third layer that is capable of limiting the diffusion of analyte as well as excluding inward diffusion of molecules with size larger than that of the analyte. The third layer is disposed on a surface of the second layer that is opposed to the surface that contacts the first layer. In an exemplary embodiment, this layer can be composed of a phase separated block copolymer with fixed amounts of hydrophobic and hydrophilic domains, permitting the diffusion of oxygen and the water soluble analyte, respectively. This layer should not be prone to swelling and should exhibit good adhesion with the aforementioned enzyme layer. In another exemplary embodiment, this layer is composed of layer-by-layer assembled polyions, small molecular weight ions (i.e. micro-cations), micelles, colloids, charged nanoparticles, nanotubes, nanowires, nanoplatlets, nanoribbons, and the like.

The fourth layer is composed of the aforementioned composite coating containing the hydrophilic matrix and the sacrificial moieties. Here, this layer must exhibit good adhesion with the aforementioned third layer. The fourth layer is disposed on a surface of the third layer that is opposed to the surface that contacts the second layer.

In order to realize calibration-free biosensor, the aforementioned outer composite coatings contain an assortment of sacrificial moieties, whose rate of degradation (and hence the rate of increase in analyte permeability via increase in fresh-void-space) matches that of the decrease in analyte permeability due to biofouling. In a variation of this methodology, bilayers and multi-layers of this sacrificial moieties loaded polymeric matrix can also be used to attain the desired rate increase in analyte permeability via increase in fresh-void-space.

This invention is also suitable for attaining internal self-calibration of the biosensor against foreign body response and biofouling. This can be achieved through differential measurement of background currents obtained from two sensing elements one of which is coated with the aforementioned sacrificial moieties-embedded polymeric matrix, while the other is blank. This differential in background currents is proportional to the magnitude of fresh-void-space and biofouling, which in turn can be used to estimate the analyte flux within the biosensor.

The biofouling inhibiting coating is exemplified by the following non-limiting examples. The invention will be illustrated in more detail with reference to the following examples, but it should be understood that the present invention is not deemed to be limited thereto.

EXAMPLES

Example 1

This example illustrates a methodology to increase analyte permeability via creation of fresh-void-space. For this example, a polymeric matrix based on hydrophilic poly(vinyl alcohol) (PVA) is used and poly(lactic-co-glycolic acid) (PLGA) (a biodegradable polymer) based microspheres are used as sacrificial moieties. These microspheres were prepared in such a way that they slowly degrade (over a period of 1-month) upon exposure to phosphate buffer saline (PBS) due to hydrolysis of its ester linkages in the presence of water. In this example, PLGA can be substituted by other biodegradable systems.

Figure 4:
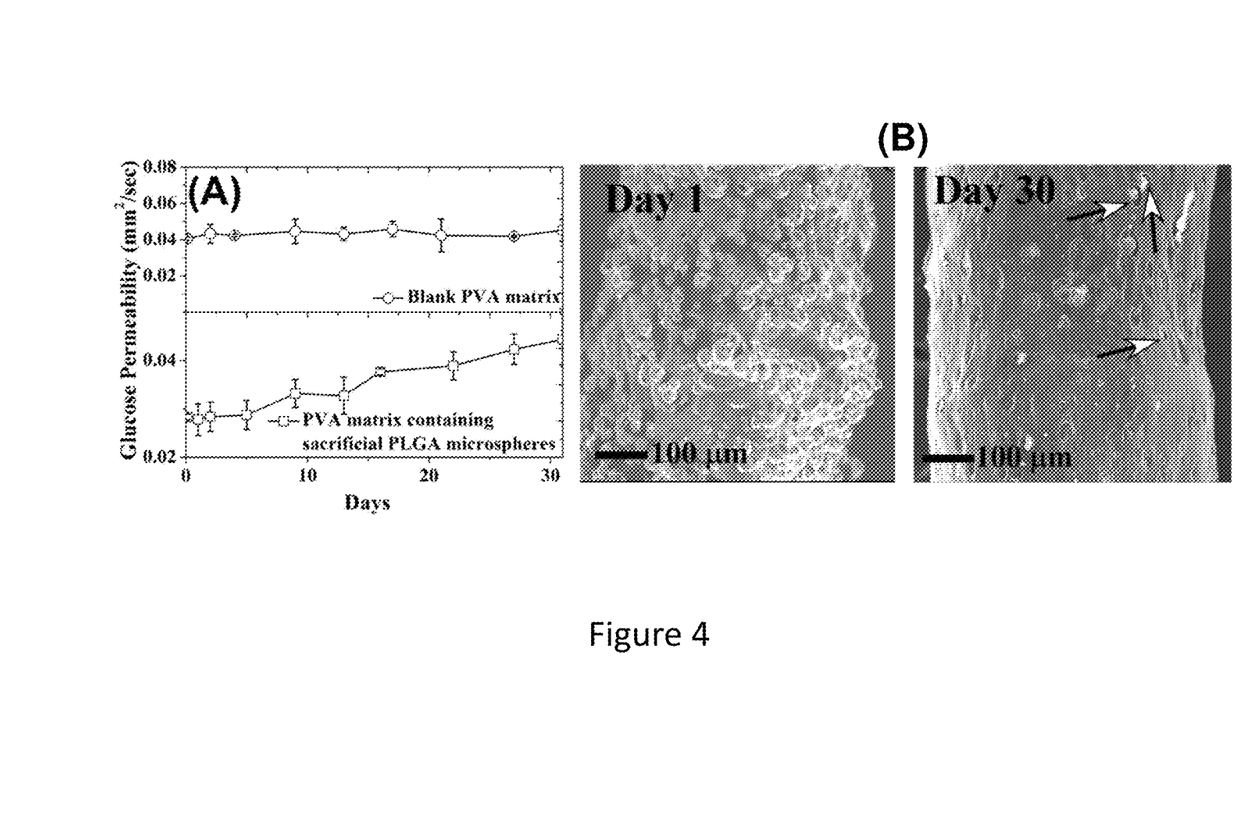
FIG. 4A shows glucose permeability through PVA polymeric matrix loaded with and without sacrificial PLGA microsphere moieties as a function of incubation in PBS buffer.
FIG. 4B shows SEM images of PVA polymeric matrix loaded with sacrificial PLGA microsphere moieties before (day 1) and after (day 30) soaking in PBS buffer.

The glucose permeability through these membranes based was monitored while the membranes were soaked in PBS for a period of 1-month, wherein the PLGA microspheres erode. As a control, membranes based on PVA matrix without the PLGA microspheres have also been used. FIG. 4A shows the glucose flux through this membrane as a function of time. As can be seen, for the blank PVA matrix, the permeability remained fairly constant after the period of one month. On the other hand, the permeability of the PVA+PLGA microsphere composite steadily increased to ca. 70% from its initial value, due to the creation of macroscopic porosity, i.e. "fresh-void-space" following the gradual degradation of the PLGA microspheres.

FIG. 4B shows the scanning electron microscopy (SEM) images of the PVA/PLGA composite membrane on day 1, which clearly shows the PLGA microspheres as well as the PVA matrix. After 30 days, the initial grainy surface of microsphere-loaded PVA hydrogel changed to a much smoother yet pitted morphology (where the microspheres were present), which indicates the creation of fresh porosity. Such fresh porosity is shown by the crevices (indicated with arrows) that are observable under certain specimen tilt. This indicates that the PVA hydrogel matrix do not completely collapse around the degraded microspheres, thereby leading to the creation of fresh-void-space.

Example 2

This example illustrates a methodology to create fresh-void-space and subsequently use it to offset the effects of biofouling. For this, a polymeric matrix based on hydrophilic poly(vinyl alcohol) (PVA) is used and poly(lactic-co-glycolic acid) (PLGA) based microspheres are used as sacrificial moieties, even though any other hydrogel and biodegradable material will also suffice. These microspheres were prepared in such a way that they will slowly degrade (over a period of 1-month) in the presence of aqueous media due to hydrolysis of its ester linkages. Membranes based on this system have been prepared and were soaked in porcine serum, which is a common biofouling media. The glucose permeability of these membranes have been determined as a function of time. Soaking in porcine serum is expected to induce biofouling on the membranes thereby decreasing its glucose permeability which is countered by the continuous creation of fresh-void-space. As a control, glucose sensors coated with PVA matrix without the PLGA microspheres have also been used.

Figure 5:
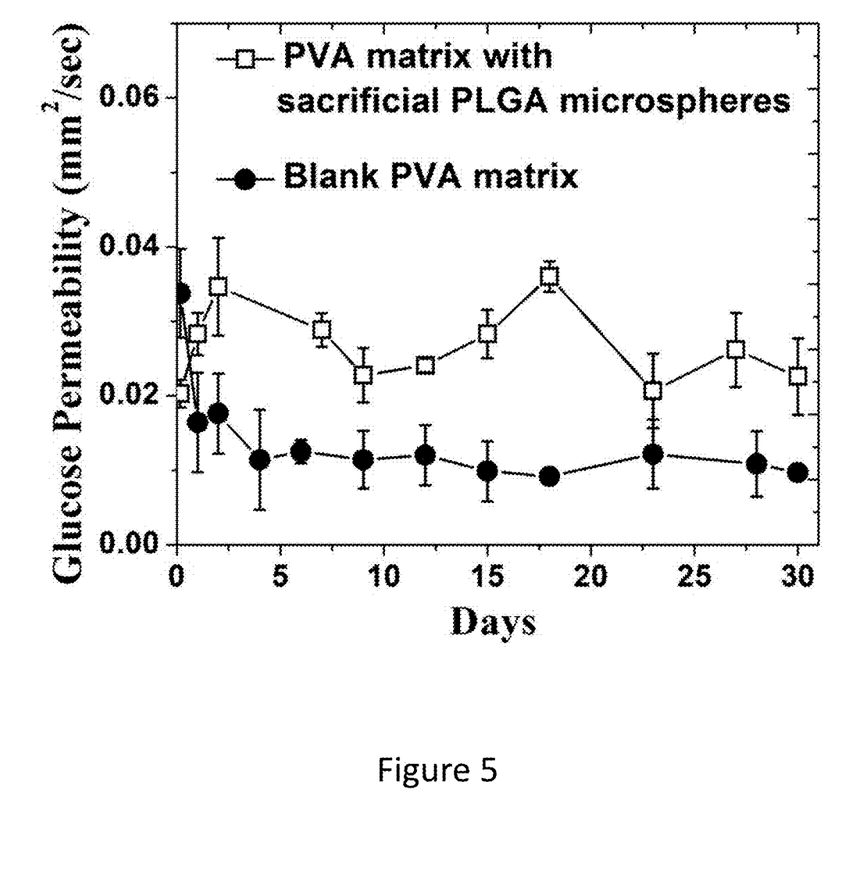
FIG. 5 shows glucose permeability through PVA polymeric matrix loaded with and without sacrificial PLGA microsphere moieties as function of incubation time in porcine serum.

FIG. 5 shows the glucose permeability through these membranes as a function of time. Exposing the control membranes (PVA matrix without the PLGA microspheres) to serum resulted in an initial rapid decrease in glucose permeability of approximately 60% (due to PVA biofouling) until day 9, after which the glucose permeability remained fairly constant. In the case of PVA matrix with the PLGA microspheres, the glucose permeability showed two cycles of permeability increase and decrease between days 0 to 9 and between days 9 to 30. The two ascending segments are associated with the creation of fresh-void-space due to erosion of sacrificial moieties (i.e. PLGA microspheres) while the two descending segments are a result of biofouling. Overall, the glucose permeability on day 30 remained the same as that of day 1 indicating the utility of fresh-void-space in countering the adverse effects of biofouling.

Example 3

This example illustrates a methodology to create fresh sensor/membrane/tissue interface as means to rupture the bound proteins, ions and cell deposits in an effort to increase analyte permeability. For this, a polymeric matrix based on hydrophilic poly(vinyl alcohol) (PVA) is used as matrix and poly(lactic-co-glycolic acid) (PLGA) based microspheres are used as sacrificial moieties, even though any other hydrogel or biodegradable microspheres can also be utilized.

These microspheres were prepared in such a way that they would slowly degrade (over a period of 1-month) in the presence of aqueous media due to hydrolysis of its ester linkages. These membranes were soaked in porcine serum, which is a common biofouling media, and were periodically imaged under SEM to assess their surface morphology. As a control, membranes based on PVA matrices without the PLGA microspheres were also used.

Figure 6:
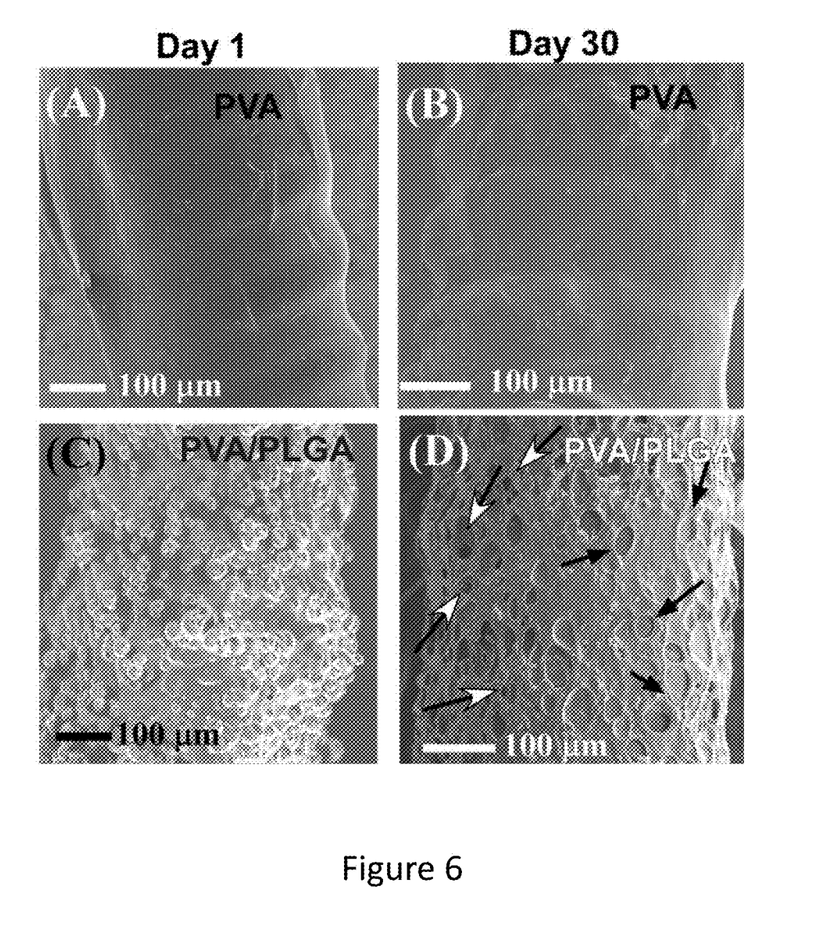
FIG. 6 shows SEM images of PVA polymeric matrix loaded with (C, D) and without (A, B) sacrificial PLGA microsphere moieties before (A, C) and after (B, D) soaking in porcine serum for a period of 1-month.

FIG. 6 shows the SEM images of these membranes on days 1 and 30. On day 1, the PVA membrane (without the sacrificial PLGA microspheres) showed a smooth surface (FIG. 6A), while the PVA/PLGA membrane displayed a grainy surface representing the embedded microspheres (FIG. 6C). Upon soaking in porcine serum, the surface of the PVA membrane became slightly rougher (FIG. 6B), indicative of the protein adsorption on the membrane surface. On the other hand, upon soaking in porcine serum, the morphology of the PVA/PLGA composite membrane changed from grainy (FIG. 6C) to a pitted/textured morphology (FIG. 6D). Moreover, a more pronounced dimple and crevice pattern is evident indicating that the serum exposed PVA coatings become rigidified (as a result of biofouling) thus preventing collapse of both dimples and crevices. The more pronounced nature of the dimples and crevices is expected to contribute to fresh sensor/tissue interface.

Example 4

This example illustrates the validity of the invented methodology as well as device in porcine serum. For this a glucose sensing element based on the architecture of the present invention has been fabricated. In line with the aforementioned description of the disclosed device, this glucose sensing element contains the following layers on top of the sensing element:

(1) A very tight, self-sealing, electropolymerized membrane of poly phenol (PPh), intended to allow diffusion of molecule smaller than $H_2O_2$ (i.e. water, oxygen, $H^+$, $OH^-$ etc.) and excluding any larger molecules from direct contact with the sensing element (i.e. working electrode).

(2) A second layer of glucose oxidase ($GO_x$) enzyme that selectively converts glucose into $H_2O_2$ (a typical electro-active specie) that will subsequently diffuse through the first layer. Upon application of 0.7 V (vs. a Ag/AgCl reference electrode) to the sensing element, the $H_2O_2$ is electro-oxidized to generate an amperometric current proportional to glucose.

(3) A third layer of polyurethane (PU) intended to limit the diffusion of glucose as well as excluding inward diffusion of molecules with size larger than that of glucose.

(4) A fourth layer is composed of the aforementioned composite coating intended to constantly generate fresh-void-space. For this coating, a polymeric matrix based on hydrophilic poly(vinyl alcohol) (PVA) is used as matrix and poly (lactic-co-glycolic acid) (PLGA) based microspheres are used as sacrificial moieties. These microspheres were prepared in such a way that they would slowly degrade (over a period of 1-month) in the presence of aqueous media due to hydrolysis of their ester linkages.

Figure 7:
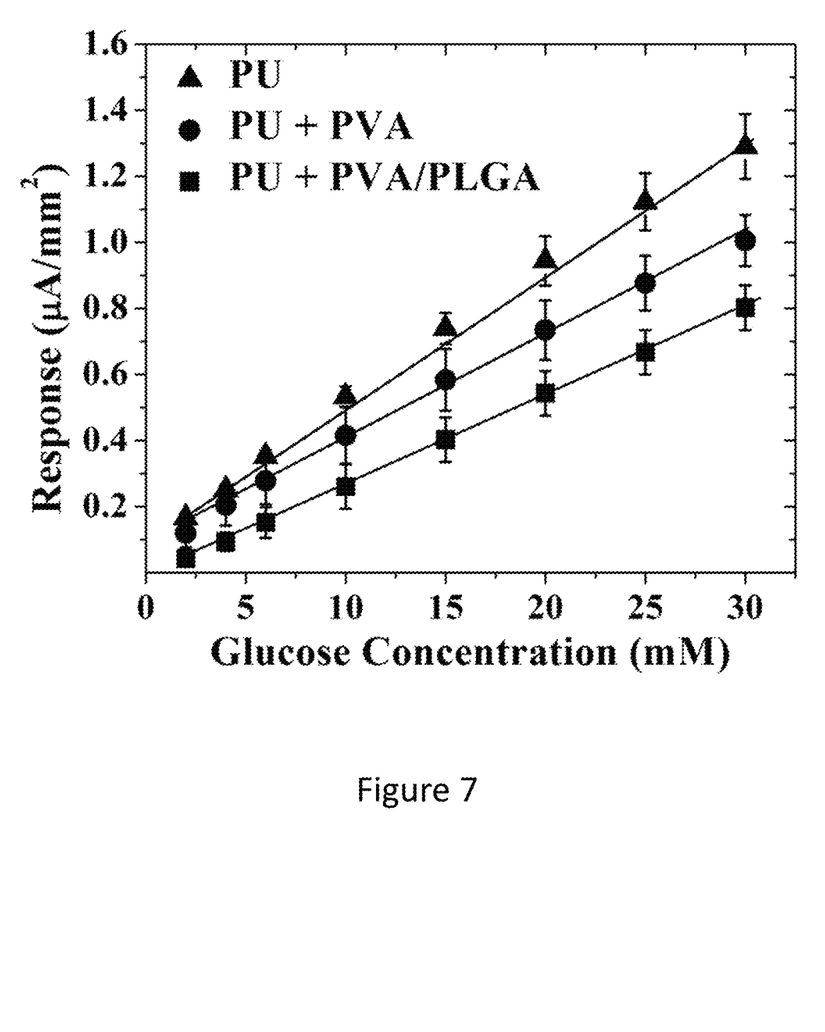
FIG. 7 shows saturation amperometric current vs. glucose concentration for a glucose sensing element containing various layers.

The sensors were initially interrogated in a non-biofouling media (PBS buffer) to deduce their performance. FIG. 7 illustrates the sensor response vs. glucose concentration for devices containing the first (PPh) and second ($GO_x$) layers in addition to (i) only polyurethane layer (herein referred as 'PU' devices);
(ii) polyurethane layer plus the fourth composite layer without the sacrificial PLGA microspheres (herein referred as 'PU+PVA' devices);
(iii) polyurethane layer plus the fourth composite layer with the sacrificial PLGA microspheres (herein referred as 'PU+PVA/PLGA' devices);

As can be seen in FIG. 7, the PU coating by itself is sufficient to impart a linear amperometric response for glucose concentrations well beyond the physiological (2 to 22 mM) range. The addition of the PVA hydrogel on top of the PU membrane did not hinder sensor linearity but slightly lowered sensor sensitivity by ca. 20%. The inclusion of PLGA microspheres within the PVA hydrogel (indicated as PU+PVA/PLGA device) resulted in a further 20% decrease in the amperometric response. These results suggest that the PVA hydrogel in its pristine form (i.e. not exposed to protein), presents a barrier to the diffusion of glucose towards the $GO_x$ enzyme, which is directly translated to sensor sensitivity.

Subsequently, the 'PU+PVA' and 'PU+PVA/PLGA' devices were soaked in either PBS (non biofouling media) or in porcine serum (a common biofouling media) and are periodically interrogated to assess their changes in glucose sensitivity.

Figure 8:
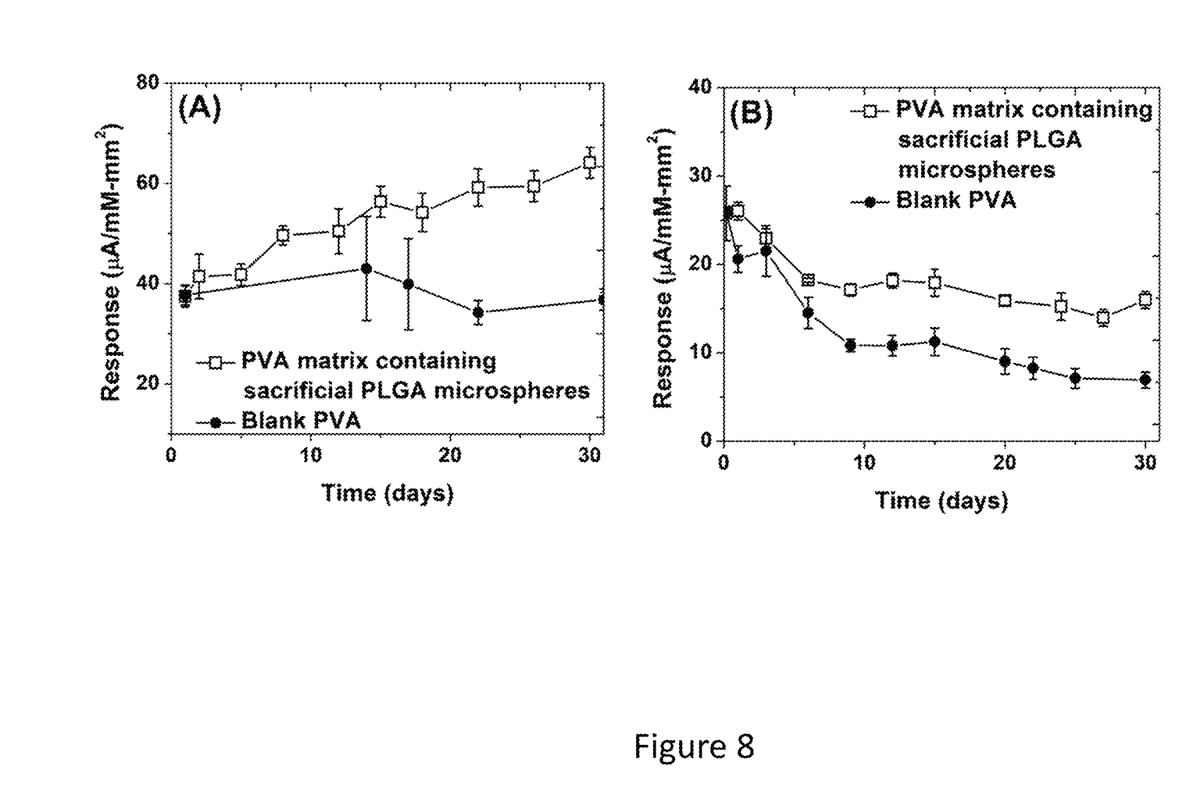
FIG. 8 shows normalized sensitivity of amperometric glucose sensors coated with PVA polymeric matrix loaded with and without sacrificial PLGA microsphere moieties as a function of soak time in PBS (A) and porcine serum (B).

FIG. 8 shows the sensitivity of glucose sensors coated with the membranes, as a function of time. When soaked in the non biofouling media (FIG. 8A), the sensitivity of PU+PVA sensors remained constant. On the other hand, the sensitivity of the PU+PVA/PLGA devices consistently increased with incubation time, eventually reaching sensitivities as high as 150% of their initial sensitivities (FIG. 8A). This is due to the degradation of PLGA microspheres, which creates fresh-void-space and increases glucose flux through the membrane.

When soaked in porcine serum (a biofouling media), the PU+PVA devices (FIG. 8B) displayed a consistent decrease in sensitivity owing to the adsorption of proteins and ions on the sensor surface that reduces glucose flux to the sensing element. The sensitivity of the PU+PVA coated sensors decreased consistently and over a period of 30 days, they lost 60% of their original sensitivity. On the other hand, the PU+PVA/PLGA devices (FIG. 6B) exhibited a significantly smaller sensitivity drop (i.e., 25% over a period of 30 days). This illustrates the efficacy of this invention towards providing means to circumvent biofouling via the creation of fresh-void-space through degradation of sacrificial moieties.

Example 5

This example shows a preferred composition for a sacrificial moiety. The preferred sacrificial moiety is composed of PLGA copolymerized with another moiety that can be rapidly cleaved. Such cleaving moiety (herein termed as "CL") is incorporated to produce an either random poly(lactic-co-glycolic-co-CL) or block (PLGA-CL)$_n$ copolymers where the individual PLGA segments possess a glass transition temperature ($T_g$) below the physiological body temperature while the entire uncleaved copolymer has a $T_g$ above body temperature. In a preferred embodiment, such cleavable moiety is composed of 4-hydroxymethyl-3-nitrobenzoic acid that can be directly incorporated within the PLGA structure (in a block or random fashion) so that it can optically degraded with the use of UV light.

In another preferred embodiment, N-tert-butoxycarbonyl-based derivatives (t-BOC derivatives) can be used to be cleaved with lowering of pH, typically realized with PLGA degradation. This will afford an auto-acceleration effect which can rapidly lower the PLGA molecular weight. In yet another embodiment, enzymatic-prone cleavage of di- and tri-phosphate derivatives can also be incorporated within the PLGA backbone. The aforementioned random or block copolymers of PLGA can be mixed with various low molecular weight compounds to accelerate the dissolution of the sacrificial moiety (low molecular weight compounds along with oligomers of lactic and glycolic acid), especially when their melting or glass transition temperature is below body temperature. In addition, these random or block copolymers of PLGA can be blended with high molecular weight PLGA of different composition to promote microphase separation within microsphere, colloidosomes, or polymersome overall morphologies. This will create porous structures that retain their overall shape due to the high molecular weight PLGA phase.

Example 6

This example illustrates a preferred composition of the sacrificial moieties containing combination of hydrophobic and hydrophilic blocks. For example, hydrophobic, biodegradable blocks can be composed of one or combinations of PLGA, PLA, PGA, polyanhydrides, polyaspirins, polylactic-glycolic acid (PLGA), poly-caprolactone (PCL), copolymers of polylactic-glycolic acid and poly-caprolactone (PCL-PLGA copolymer), polyhydroxy-butyrate-valerate (PHBV), polyorthoester (POE), polyethylene oxide-butylene terephthalate (PEO-PBTP), and poly-D,L-lactic acid-p-dioxanone-polyethylene glycol block copolymer (PLA-DX-PEG).

Examples of the hydrophilic polymers are polyacrylates, polyacrylamides, polyvinylacetates, polyvinyl acetamides, polyvinyl alcohols, neutralized and un-neutralized polymeric acids (e.g., neutralized and un-neutralized polyacrylics acids, neutralized and un-neutralized polysulfonic acids, neutralized and un-neutralized polystyrene sulfonic acids, or the like) polydiallyl dimethyl ammonium chlorides, poly(1-glycerol methacrylate)s, poly(2-dimethylaminoethyl methacrylate)s, poly(2-ethyl-2-oxazoline), poly(2-hydroxyethyl methacrylate/methacrylic acid)s, poly(2-hydroxypropyl methacrylate)s, poly(2-methacryloxyethyltrimethylammonium halide)s, poly(2-vinyl-1-methylpyridinium halide)s, poly(2-vinylpyridine N-oxide)s, poly(2-vinylpyridine)s, poly(3-chloro-2-hydroxypropyl-2-methacryloxyethyldimethylammonium chloride)s, or the like, or a combination comprising at least one of the foregoing water soluble polymers.

In one embodiment, the polymer can comprise one or more of the foregoing water soluble polymers and a synthetic polymer that is hydrophobic so long as the resulting polymer is swellable in the carrier fluid. In an exemplary embodiment, the polymer can comprise one or more of the foregoing water soluble polymers and a synthetic polymer that is hydrophobic so long as the resulting polymer is swellable in an aqueous carrier fluid. The foregoing water soluble polymers can be copolymerized or blended with the hydrophobic synthetic polymer.

Examples of hydrophobic synthetic polymers are polyacetals, polyolefins, polycarbonates, polystyrenes, polyesters, polyamides, polyamideimides, polyarylates, polyarylsulfones, polyethersulfones, polyphenylene sulfides, polyvinyl chlorides, polysulfones, polyimides, polyetherimides, polytetrafluoroethylenes, polyetherketones, polyether etherketones, polyether ketone ketones, polybenzoxazoles, polyphthalides, polyacetals, polyanhydrides, polyvinyl ethers, polyvinyl thioethers, polyvinyl ketones, polyvinyl halides, polyvinyl nitriles, polyvinyl esters, polysulfonates, polysulfides, polythioesters, polysulfones, polysulfonamides, polyureas, polyphosphazenes, polysilazanes, polyethylene terephthalate, polybutylene terephthalate, polyurethane, polytetrafluoroethylene, polychlorotrifluoroethylene, polyvinylidene fluoride, polyoxadiazoles, polybenzothiazinophenothiazines, polybenzothiazoles, polypyrazinoquinoxalines, polypyromellitimides, polyquinoxalines, polybenzimidazoles, polyoxindoles, polyoxoisoindolines, polydioxoisoindolines, polytriazines, polypyridazines, polypiperazines, polypyridines, polypiperidines, polytriazoles, polypyrazoles, polypyrrolidines, polycarboranes, polyoxabicyclononanes, polydibenzofurans, polyphtalides, polyacetals, polyanhydrides, polyvinyl ethers, polyvinyl thioethers, polyvinyl ketones, polyvinyl halides, polyvinyl nitriles, polyvinyl esters, polysulfonates, polysulfides, polythioesters, polysulfones, polysulfonamides, polyureas, polyphosphazenes, polysilazanes, polysiloxanes, polyolefins, or the like, or a combination comprising at least one of the foregoing hydrophobic synthetic polymers.

This invention may be embodied in many different forms, and should not be construed as limited to the embodiments set forth herein. Rather, these embodiments are provided so that this disclosure will be thorough and complete, and will fully convey the scope of the invention to those skilled in the art. Like reference numerals refer to like elements throughout.

The terminology used herein is for the purpose of describing particular embodiments only and is not intended to be limiting. As used herein, the singular forms "a," "an" and "the" are intended to include the plural forms as well, unless the context clearly indicates otherwise. It will be further understood that the terms "comprises" and/or "comprising," or "includes" and/or "including" when used in this specification, specify the presence of stated features, regions, integers, steps, operations, elements, and/or components, but do not preclude the presence or addition of one or more other features, regions, integers, steps, operations, elements, components, and/or groups thereof.

Unless otherwise defined, all terms (including technical and scientific terms) used herein have the same meaning as commonly understood by one of ordinary skill in the art to which this disclosure belongs. It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

The transition term "comprising" is inclusive of the transition terms "consisting of" and "consisting essentially of".

All numerical ranges included herein are interchangeable and are inclusive of end points and all numerical values that lie between the endpoints.

The terms "decompose", "degradation" and/or "degradable" refer to the conversion of materials into smaller components, intermediates, or end products.

The term and/or is used herein to mean both "and" as well as "or". For example, "A and/or B" is construed to mean A, B or A and B.

While the invention has been described in detail in connection with a number of embodiments, the invention is not limited to such disclosed embodiments. Rather, the invention can be modified to incorporate any number of variations, alterations, substitutions or equivalent arrangements not heretofore described, but which are commensurate with the scope of the invention. Additionally, while various embodiments of the invention have been described, it is to be understood that aspects of the invention may include only some of the described embodiments. Accordingly, the invention is not to be seen as limited by the foregoing description, but is only limited by the scope of the appended claims.

What is claimed is:

1. A device comprising:
   a biosensor having disposed upon it a coating; the coating comprising:
   a polymer matrix; where the polymer matrix is operative to facilitate an inwards and outwards diffusion of analytes, byproducts and other water soluble entities towards a sensing element of the biosensor; and
   a sacrificial moiety; the sacrificial moiety being dispersed in the polymer matrix, where the sacrificial moiety erodes with time and increases the porosity of the polymer matrix thus offsetting decreases in analyte permeability as a result of biofouling,
   where the polymer matrix comprises hydrogels, xerogels, organogels, absorbent polymers, dip-coated or layer-by-layer coated polyelectrolytes, electropolymerized polymers, or combinations thereof.

2. The device of claim 1, where the erosion of sacrificial moieties creates a new implantable device-tissue interface; the new implantable device-tissue interface presenting a fresh surface to biofouling media to re-establish analyte transport within the polymeric matrix.

3. The device of claim 1, where the polymeric matrix experiences a 'partial' or 'no' collapse following the erosion of the sacrificial moieties.

4. The device of claim 1, where the sacrificial moieties comprise a biodegradable polymer.

5. The device of claim 4, where the biodegradable polymer is a polyanhydride, polyaspirin, polylactic-glycolic acid, poly-caprolactone, copolymers of polylactic-glycolic acid and poly-caprolactone, polyhydroxy-butyrate-valerate, polyorthoester, polyethylene oxide-butylene terephthalate, poly-D,L-lactic acid-p-dioxanone-polyethylene glycol block copolymer, or a combination thereof.

6. The device of claim 1, where the sacrificial moiety comprises an amphiphilic block copolymer.

7. The device of claim 1, where the amphiphilic block copolymer comprises a hydrophilic block and a hydrophobic block; the hydrophilic block being selected from the group consisting of polyacrylates, polyacrylamides, polyvinylacetates, polyvinyl acetamides, polyvinyl alcohols, neutralized and un-neutralized polymeric acids, neutralized and un-neutralized polyacrylics acids, neutralized and un-neutralized polysulfonic acids, neutralized and un-neutralized polystyrene sulfonic acids, polydiallyl dimethyl ammonium chlorides, poly(l-glycerol methacrylate)s, poly(2-dimethylaminoethyl methacrylate)s, poly(2-ethyl-2-oxazoline), poly(2-hydroxyethyl methacrylate/methacrylic acid)s, poly(2-hydroxypropyl methacrylate)s, poly(2-methacryloxyethyltrimethylammonium halide)s, poly(2-vinyl-1-methylpyridinium halide)s, poly(2-vinylpyridine N-oxide)s, poly(2-vinylpyridine)s, poly(3-chloro-2-hydroxypropyl-2-methacryloxyethyldimethylammonium chloride)s, polysaccharides, derivatives of polysaccharides, hydroxyethyl guar, carboxymethyl guar, carboxyethyl guar, carboxymethyl hydroxypropyl guar, cellulose, cellulose derivatives, derivatives of cellulose, hydroxyethylcellulose, hydroxypropylcellulose, carboxymethylcellulose, carboxyethylcellulose, carboxymethyl hydroxyethyl cellulose, carboxymethyl hydroxypropyl cellulose, karaya, locust bean, pectin, tragacanth, acacia, carrageenan, alginates, salts of alginate, propylene glycol alginate, agar, gellan, xanthan, scleroglucan, and a combination thereof and the hydrophobic block being selected from the group consisting of polyacetals, polyolefins, polycarbonates, polystyrenes, polyesters, polyamides, polyamideimides, polyarylates, polyarylsulfones, polyethersulfones, polyphenylene sulfides, polyvinyl chlorides, polysulfones, polyimides, polyetherimides, polytetrafluoroethylenes, polyetherketones, polyether etherketones, polyether ketone ketones, polybenzoxazoles, polyphthalides, polyacetals, polyanhydrides, polyvinyl ethers, polyvinyl thioethers, polyvinyl ketones, polyvinyl halides, polyvinyl nitriles, polyvinyl esters, polysulfonates, polysulfides, polythioesters, polysulfones, polysulfonamides, polyureas, polyphosphazenes, polysilazanes, polyethylene terephthalate, polybutylene terephthalate, polyurethane, polytetrafluoroethylene, polychlorotrifluoroethylene, polyvinylidene fluoride, polyoxadiazoles, polybenzothiazinophenothiazines, polybenzothiazoles, polypyrazinoquinoxalines, polypyromellitimides, polyquinoxalines, polybenzimidazoles, polyoxindoles, polyoxoisoindolines, polydioxoisoindolines, polytriazines, polypyridazines, polypiperazines, polypyridines, polypiperidines, polytriazoles, polypyrazoles, polypyrrolidines, polycarboranes, polyoxabicyclononanes, polydibenzofurans, polyphtalides, polyacetals, polyanhydrides, polyvinyl ethers, polyvinyl thioethers, polyvinyl ketones, polyvinyl halides, polyvinyl nitriles, polyvinyl esters, polysulfonates, polysulfides, polythioesters, polysulfones, polysulfonamides, polyureas, polyphosphazenes, polysilazanes, polysiloxanes, polyolefins, and a combination thereof.

8. The device of claim 1, where the erosion of the sacrificial moieties occurs when exposed to physiological fluids.

9. The device of claim 1, where the erosion of the sacrificial moieties occurs by localized heat, changes in pH, light irradiation, ultrasound, or combinations thereof.

10. The device of claim 9, where said changes in pH are achieved by cleaving N-tert-butoxycarbonyl-based derivatives (t-BOC derivatives) present in the said sacrificial moieties.

11. The device of claim 1, where the sacrificial moieties are colloidosomes comprising a biodegradable polymeric bead or a labile group, wherein an inner hollow core is surrounded by hydrophobic bead like structures.

12. The device of claim 1, where the said sacrificial moieties are polymersomes comprising a biodegradable polymeric bead.

13. The device of claim 12, where the polymersomes contain nano- or micro-crystals within their outer shell.

14. The device of claim 12, where the polymersomes have an outer shell that is a biodegradable hydrophobic polymer and the inner core is a dried hydrophilic polymer.

15. The device of claim 1, where the coating increases porosity in proportion to a decrease in permeability from the said biofouling.

16. The device of claim 12, where the polymersome have an outer shell that comprises a biodegradable hydrophobic polymer and an inner core that comprises a dried hydrophilic polymer.

17. The device of claim 12, where the said polymersomes contain an assortment of polymer-coated reactive species within their shell that release gases upon degradation of polymersomes.

18. The device of claim 1, where the sacrificial moieties are selected from the group consisting of polymersomes, colloidosomes, polymeric microspheres, block copolymers, interpenetrating networks, filled composites, polymer coated nanoparticles, nanoplatlets, nanorods, polymer coated salt crystals, self-assembled polymer spheres, and combinations thereof.

19. A method of manufacturing a biosensor comprising:
disposing a coating on a biosensor; the coating comprising:
a polymer matrix; where the polymer matrix is operative to facilitate an inwards and outwards diffusion of analytes and byproducts to and from the sensing element of the biosensor; and
a sacrificial moiety; the sacrificial moiety being dispersed in the polymer matrix, where the sacrificial moiety erodes with time and increases the porosity of the polymer matrix thus offsetting decreases in analyte permeability as a result of biofouling,
where the polymer matrix comprises hydrogels, xerogels, organogels, absorbent polymers, dip-coated or layer-by-layer coated polyelectrolytes, electropolymerized polymers, or combinations thereof.

20. An analyte-sensing device capable of reliable sensing in a biofouling-prone media comprising:
a sensing element;
a self sealing layer disposed on the sensing element capable of allowing diffusion of electro-active species towards the sensing element; where the self sealing layer is not prone to swelling and is intimately bonded to the sensing element;
one or more layers comprising enzymes that are disposed upon the self-sealing layer; selectively the enzymes being operative to convert an analyte of interest to an electro-active species; where the electro-active species diffuses through the self sealing layer to produce a detectable signal proportional to a concentration of the analyte;
a second layer disposed upon the one or more layers that comprises enzymes; the second layer being operative to limit diffusion of the analyte and control diffusion towards the sensor of molecules with size larger than that of the analyte;
a third layer comprising a composite coating that comprises a polymer matrix and a sacrificial moiety; where the polymer matrix is operative to facilitate the inwards and outwards diffusion of analytes and byproducts to and from the sensing element; and wherein the sacrificial moiety is dispersed in the polymer matrix, where the sacrificial moiety erodes with time and increases the porosity of the polymer matrix thus offsetting decreases in analyte permeability as a result of biofouling.

21. The device of claim 20, where the electro-active specie is one of $H_2O_2$, $OH^-$, $H^+$, $O_2$ and NO.

22. The device of claim 21, where the sensing element is a working electrode of an electrochemical sensor.

23. The device of claim 22, where the said sensing element senses a change in one or more of amperometric, potentiometric, voltammetry, optical, magnetic, piezoelectric, electronic, piezostrictive, magnetostrictive, electromagnetic, photonic, or impedance changes.

24. A method to realize an internal self-calibration of an implantable biosensor, the biosensor comprising:
two sensing elements; where self calibration of the biosensor is achieved through differential measurement of background currents obtained from the two sensing elements; where one of the sensing elements is encased in an outer composite membrane, while the other of the said sensing element is intentionally left blank; the said outer composite membrane comprises a polymer matrix and a sacrificial moiety; where the polymer matrix is operative to facilitate an inwards diffusion of analytes towards the sensing element; and wherein the sacrificial moiety is dispersed in the polymer matrix, where the sacrificial moiety erodes with time and increases the porosity of the polymer matrix thus offsetting decreases in analyte permeability as a result of biofouling,
where the polymer matrix comprises hydrogels, xerogels, organogels, absorbent polymers, dip-coated or layer-by-layer coated polyelectrolytes, electropolymerized polymers, or combinations thereof.

25. A device comprising:
a biosensor having disposed upon it a coating; the coating comprising:
a polymer matrix; where the polymer matrix is operative to facilitate an inwards and outwards diffusion of analytes, byproducts and other water soluble entities towards a sensing element of the biosensor; and
a sacrificial moiety; the sacrificial moiety being dispersed in the polymer matrix, where the sacrificial moiety erodes with time and increases the porosity of the polymer matrix thus offsetting decreases in analyte permeability as a result of biofouling,
where the erosion of the sacrificial moieties occurs by localized heat, changes in pH, light irradiation, ultrasound, or combinations thereof, and said changes in pH are achieved by cleaving N-tert-butoxycarbonyl-based derivatives (t-BOC derivatives) present in the said sacrificial moieties.

26. A method of manufacturing a biosensor comprising:
disposing a coating on a biosensor; the coating comprising:
a polymer matrix; where the polymer matrix is operative to facilitate an inwards and outwards diffusion of analytes and byproducts to and from the sensing element of the biosensor; and
a sacrificial moiety; the sacrificial moiety being dispersed in the polymer matrix, where the sacrificial moiety erodes with time and increases the porosity of the polymer matrix thus offsetting decreases in analyte permeability as a result of biofouling,
where the erosion of the sacrificial moieties occurs by localized heat, changes in pH, light irradiation, ultrasound, or combinations thereof, and said changes in pH are achieved by cleaving N-tert-butoxycarbonyl-based derivatives (t-BOC derivatives) present in the said sacrificial moieties.

27. A method to realize an internal self-calibration of an implantable biosensor, the biosensor comprising:
two sensing elements; where self calibration of the biosensor is achieved through differential measurement of background currents obtained from the two sensing elements; where one of the sensing elements is encased in an outer composite membrane, while the other of the said sensing element is intentionally left blank; the said outer composite membrane comprises a polymer matrix and a sacrificial moiety; where the polymer matrix is operative to facilitate an inwards diffusion of analytes towards the sensing element; and wherein the sacrificial moiety is dispersed in the polymer matrix, where the sacrificial moiety erodes with time and increases the porosity of the polymer matrix thus offsetting decreases in analyte permeability as a result of biofouling,
where the erosion of the sacrificial moieties occurs by localized heat, changes in pH, light irradiation, ultrasound, or combinations thereof, and said changes in pH are achieved by cleaving N-tert-butoxycarbonyl-based derivatives (t-BOC derivatives) present in the said sacrificial moieties.

* * * * *